US009155506B2

(12) United States Patent
Spies

(10) Patent No.: US 9,155,506 B2
(45) Date of Patent: Oct. 13, 2015

(54) METHOD AND SYSTEM FOR PROCESSING MRT DATA OF THE HUMAN BRAIN

(71) Applicant: jung diagnostics GmbH, Hamburg (DE)

(72) Inventor: Lothar Spies, Hamburg (DE)

(73) Assignee: jung diagnostics GmbH, Hamburg (DE)

( * ) Notice: Subject to any disclaimer, the term of this patent is extended or adjusted under 35 U.S.C. 154(b) by 141 days.

(21) Appl. No.: 13/897,755

(22) Filed: May 20, 2013

(65) Prior Publication Data

US 2013/0317341 A1    Nov. 28, 2013

(30) Foreign Application Priority Data

May 23, 2012    (DE) .......................... 10 2012 208 625

(51) Int. Cl.
| | |
|---|---|
| A61B 5/00 | (2006.01) |
| A61B 5/055 | (2006.01) |
| G06T 7/00 | (2006.01) |
| G01R 33/56 | (2006.01) |

(52) U.S. Cl.
CPC ............... *A61B 5/7271* (2013.01); *A61B 5/055* (2013.01); *G06T 7/0014* (2013.01); *G01R 33/5608* (2013.01); *G06T 2207/10088* (2013.01); *G06T 2207/30016* (2013.01)

(58) Field of Classification Search
CPC .. A61B 5/7271; A61B 5/055; G01R 33/5608; G06T 2207/10088; G06T 2207/30016; G06T 7/0014
USPC ............ 600/410, 411, 416; 128/922; 382/128
See application file for complete search history.

(56) References Cited

U.S. PATENT DOCUMENTS

| | | |
|---|---|---|
| 6,366,797 B1 | 4/2002 | Fisher et al. |
| 8,112,144 B2 | 2/2012 | Yamamoto et al. |

OTHER PUBLICATIONS

Mehta et al., NeuroImage 20 (2003), pp. 1438 to 1454, "Evaluation of voxel-based morphometry for focal lesion detection in individuals".
Stamatakis et al., Brain and Language 94 (2005), pp. 167-177, "Identifying lesions on structural brain images—Validation of the method and application to neuropsychological patients".
De Boer et al., NeuroImage 45 (2009) pp. 1151-1161, "White matter lesion extension to automatic brain tissue segmentation on MRI".
Ashburner et al., NeuroImage 26 (2005), pp. 839 to 851, "Unified segmentation".

(Continued)

*Primary Examiner* — Michael Rozanski
(74) *Attorney, Agent, or Firm* — Rankin, Hill & Clark LLP

(57) ABSTRACT

A method, a software program and a system for processing MRT data of the human brain of a patient, wherein three-dimensional MRT data resolved in voxels of the patient's brain and the brains of a normative database of a plurality of neurologically healthy human individuals are available. The MRT data of the patient's brain are segmented for each voxel into portions of grey substance, white substance and liquor by means of a classification algorithm, wherein for comparison with corresponding data of the normative database the data are normalized before, after or synchronously into a standardized stereotactic space whereby one or more normalized tissue maps result that contain the proportions determined by the classification algorithm, and the tissue map or tissue maps of the patient's brain is or are subjected to a voxel-wise statistical comparison with the correspondingly normalized and segmented data of the normative database.

17 Claims, 4 Drawing Sheets

Patient

Normal

(56) References Cited

OTHER PUBLICATIONS

Seghier et al., "Lesion identification using unified segmentation-normalisation models and fuzzy clustering", NeuroImage 41 (2008), 1253-1266.

Good, Cartiona et al.; "A Voxel-Based Morphometric Study of Ageing in 465 Normal Adult Human Brains;" NeuroImage 14:21-36; Academic Press, Published online May 11, 2001.

Boelmans, Kai et al.; "A novel computerized algorithm to detect microstructural brainstem pathology in Parkinson's disease using standard 3 Tesla MR imaging;" J Neurol 261:1968-75; Springer-Verlag Berlin Heidelberg; Published online Jul. 26, 2014.

stereotactically normalized

Patient Normal

METHOD AND SYSTEM FOR PROCESSING MRT DATA OF THE HUMAN BRAIN

BACKGROUND OF THE INVENTION

1. Field of the Invention

The invention relates to a method, a software program and a system for processing MRT data of the human brain of a patient, wherein three-dimensional MRT data resolved in voxels of the patient's brain and the brains of a normative database of a plurality of neurologically healthy human individuals are available.

The investigation of magnetic resonance tomography data (MRT) of human brains with degenerative symptoms such as lesions is an important tool in the medical examination of human brains. Corresponding automated or semiautomated methods that permit statistical examinations of three-dimensional MRT data are known. Their results provide the diagnosing physician with criteria for his diagnosis.

2. Description of Related Art

Various approaches are followed for corresponding automated, or partially automated, raw-data-based examination methods. A first known method is to perform a voxel-based morphometry of the brain of the patient. The voxel-based morphometry consists of classifying the individual volume elements (voxels) of the MRT data of the brain into categories of grey matter or respectively substance (GM), white matter or respectively substance (WM), and cerebrospinal fluid or liquor (CSF) by means of a segmentation or respectively categorization algorithm. The different signals that these different substances in the brain emit as a reaction to the MRT scan are used to distinguish the different tissue classes. Typical voxel sizes of modern MRT scanners are cubical or rectangular-cubical space elements with edge lengths of one to two millimeters and a volume of 1 to 8 mm$^3$.

In Mehta et al., NeuroImage 20 (2003), pages 1438 to 1454, "Evaluation of voxel-based morphometry for focal lesion detection in individuals," a corresponding voxel-based morphometry is presented for focal lesion detection in individuals, wherein contours manually determined by an expert are used as a basis for comparison (also termed "ground truth"). A method is thereby assessed in regard to its ability to automatically determine the contours of lesions. A deficiency or deficit of white and grey substance is looked for since lesions always cause a decrease in the detected white substance or respectively grey substance where white substance or respectively grey substance should be dominant.

In Stamatakis et al., Brain and Language 94 (2005), pages 167-177, "Identifying lesions on structural brain images— Validation of the method and application to neuropsychological patients," a variety of known segmentation or respectively categorization algorithms were applied to the MRT data of damaged brains with lesions. It was found that these do not function satisfactorily for existing lesions. It was therefore proposed to instead compare the smoothed, non-segmented MRT data of a patient's brain with the data of a control group in order to identify and mark lesions.

According to de Boer et al., NeuroImage 45 (2009), pages 1151-1161, "White matter lesion extension to automatic brain tissue segmentation on MRI,", the insufficient suitability of known categorization algorithms in the presence of lesions was circumvented by using T2-weighted or FLAIR scans (fluid attenuated inversion recovery) in which lesions appear hyperintense in the white substance in addition to the known segmentation of T1-weighted scans. These are used to define a fourth tissue class, so-called "white matter lesions" (WML). These WML regions are no longer subjected to the known segmentation into WM, GM and CSF.

U.S. Pat. No. 6,366,797 B1 discloses a method for analyzing medical data, particularly MRT scans. A volume of the brain is determined that excludes liquor-filled regions. The brain volume is normalized with reference to a full contour volume so that a parenchymal fraction of the brain is generated. This serves as a measure of cerebral atrophy and helps determine the severity and progression of multiple sclerosis or other clinical pictures that lead to neurodegeneration or axonal damage.

U.S. Pat. No. 8,112,144 B2 relates to a method for visualizing cerebral atrophies. Asymmetries are exploited that result from cerebral atrophies arising on one side. The relations of the grey substance and white substance in the left and corresponding right hemispheres of the brain are compared with each other, and statistically significant differences are visualized.

The aforementioned methods are able to identify lesions or atrophies of the brain to varying degrees.

BRIEF SUMMARY OF THE INVENTION

It is in contrast the object of the invention to provide the diagnosing physician with preprocessed information that simplifies the corresponding diagnosis for him, wherein a method, a system and a software program are to be provided by means of which MRT data of the human brain of a patient can be processed so that statistically significant and possibly quantifiable data on changes in the patient's brain are determined and depicted.

The object is achieved by a method for processing MRT data of the human brain of a patient, wherein three-dimensional MRT data resolved in voxels (volume elements) of the patient's brain and the brains of a normative database of a plurality of neurologically healthy human individuals are available, wherein the MRT data of the patient's brain are segmented for each voxel into portions of grey substance, white substance and liquor by means of a classification algorithm, the data to be compared with corresponding data of the normative database are transformed into a standardized stereotactic space, resulting in one or more normalized tissue maps that contain the proportions determined by the classification algorithm. The transformation occurs before, after or synchronous with segmentation, and the tissue map or tissue maps of the patient's brain is or are subjected to a voxel-wise statistical comparison with the correspondingly normalized and segmented data of the normative database.

The method according to the invention is characterized in that the voxel-wise statistical comparison of the tissue map, or tissue maps, is a morphometric comparison, wherein those statistically significant voxels in the tissue map, or tissue maps, of the patient's brain are identified that belong to a region dominated by the white substance that contains more grey substance than should be expected from the normative database, or that belong to a region dominated by the grey substance that contains more white substance than would be expected from the normative database.

The MRT data are preferably T1-weighted MRT data. Classification or respectively segmentation algorithms are known. Various examples of this are cited in Stamatakis et al., Brain and Language 94 (2005), pages 167-177. A suitable algorithm can be selected from the known classification algorithms in order to implement the invention.

For optimum comparability, the MRT data of the normative database have preferably been generated with the same device that was used for the patient's brain. Other data which has been standardized, such as published data, can also be used.

The characterization of statistically significant voxels is to be understood as graphic highlighting, framing of clusters of corresponding voxels, marking in a data field of the tissue map or tissue maps, data entries on the statistical significance of the deviation, or another suitable characterization by means of which the corresponding voxels can be identified.

This method according to the invention constitutes a novel bio-marker for marking degenerative regions of the brain on the basis of the known voxel-based classification of MRT data into grey substance, white substance and cerebrospinal fluid. Stereotactically normalized tissue maps of the different substances are produced. A corresponding tissue map can also be a four-dimensional matrix in which the three dimensions correspond to the X, Y, and Z coordinates of space, and the fourth dimension has three entries for the percentage of grey substance, white substance and cerebrospinal fluid. The expression "tissue map" can consequently stand for an all-encompassing four-dimensional matrix, or a four-dimensional data array, as well as individual three-dimensional data arrays or matrices.

The segmented data, the so-called tissue maps of the patient's brain categorized according to GM, WM and CSF, are statistically compared with corresponding tissue maps of the normative database. A statistical distribution may be calculated, for example with an average and standard deviation, of the percentages of grey substance, white substance and cerebrospinal fluid per voxel from the tissue maps of the comparative data, and the calculated percentages in the patient's brain may be compared therewith, and statistically significant deviations marked up.

The criterion of statistical significance can be expressed as the significance of the deviation from the normative database. For example, a deviation of $3\sigma$ or more, or $4\sigma$ or more, can be defined as statistically significant. When a one-sided t-test is employed, a probability of $p<0.05$, $p<0.01$, $p<0.001$ or thresholds that are even lower can be assumed.

This procedure that differs from the previously cited known methods exploits the fact that damaged regions of the brain cannot be clearly assigned to the grey substance or white substance in the MRT scan. The damaged substance, especially in the case of lesions, appears in the MRT data with values lying between the white and grey substance. However, instead of defining a fourth tissue type to which these regions can be assigned or employing other T2-weighted or FLAIR scans as is known in the prior art, a classic segmentation into white substance, grey substance and cerebrospinal fluid is performed for these regions according to the invention, which necessarily leads to misclassifications. For example, grey substance is partially identified as white substance, or vice versa, in the damaged regions since the segmentation algorithm or respectively classification algorithm is not adapted to this damaged type of tissue. This misclassification is used statistically.

The brain is quite clearly divided into different regions in which the white substance or grey substance dominates, i.e., comprises more than 70% or 80% of the brain matter proportion in the region, whereas the other substance constitutes a smaller minority share. In this case, misclassifications cause the minority substance to be overestimated and the majority substance to be underestimated. The ground truth is less for the minority substance than for the majority substance so that a certain absolute overestimate generates a large relatively shift in the minority component. This correspondingly provides a statistically significant measure of the misclassification, and hence the damage, in the region in which the white substance or grey substance predominates.

This effect is independent of whether the white or grey substance is considered the majority component. According to the invention, the excess of the minority substance is preferably considered.

The cerebrospinal fluid plays a minor or no role since it distinctly differs from the white substance as well as the grey substance and the damaged regions in the white and grey substance in the MRT data, and scarcely contributes to misclassification.

In addition, it can also preferably be provided to identify such statistically significant voxels in the tissue map, or tissue maps, of the patient's brain that belong to a region dominated by the white substance in which less white substance is contained than is to be expected from the normative database, or that belong to the region dominated by the grey substance in which less grey substance is contained than is to be expected from the normative database.

The related tests that are performed are preferably t-tests that determine the probability of the statistical relevance of a value's deviation from a normal distribution. This is, in particular, a one-sided two sample t-test.

Preferably, coherent clusters of statistically significant voxels are measured with respect to their volume, and/or are counted, and/or are depicted as a histogram. This offers a quantification and/or a visual depiction of the morphometric, statistical result of the examination.

To suppress statistical fluctuations, it is advantageously provided to smooth the segmented MRT data to create the tissue map or tissue maps. This can for example be done by using Gaussian filters for a plurality of voxels so that the size of the Gaussian filter is 6 to 8 mm.

The method according to the invention is preferably performed in the region in which either the white substance or the grey substance predominates, wherein dominance is defined as a proportion of 70% or more, in particular 80% or more, of white or respectively grey substance for the respective voxel.

The patterns arising from the statistical test, or statistical tests, are preferably depicted as an image, particularly in an overlay of the MRT data or segmented data of the patient's brain.

It is also advantageous to interpolate the voxels of the tissue map or tissue maps to form regular or irregular grids.

The method according to the invention is advantageously prepared by iteratively adjusting the parameters of the classification algorithm to reproduce the published results for the MRT data of the normative database and/or to finely adjust to a ground truth (comparative quantity) of simulated data, wherein the classification algorithm for the statistical tests is used with the same parameters for the MRT data from the normative database as well as from the patient's brain. This ensures uniform processing and a statistical assessment of the collected data and data from the patient's brain.

In addition, one or more volumetric tests are advantageously performed in which the volumes of white and grey substance can be calculated from the tissue maps using masks for the regions of the patient's brain being examined. These volumetric tests are supportive of the statistical tests that are also performed according to the invention. Corresponding regions of the patient's brain to be examined are the brain stem, cerebellum, corpus callosum and/or the regions of the frontal, parietal, occipital and/or temporal lobe. This yields excesses or deficits relative to the volumes that would be expected from the normative database, and these can also be compared with each other. Excesses in the respective minority component are highly statistically significant.

The volumes are preferably adapted to the individual data of the patient by means of a correction with respect to a covariate, or a plurality of covariates, in particular head size, age, duration of illness and/or gender, and/or are standardized to the overall brain substance, overall white or grey substance, or total intracranial volume, wherein the standardized volumes are in particular corrected for age. This enhances comparability. In particular, published results on average volumes as a function of the covariate are employed to minimize distorting effects that may result when the data from the normative database do not, or only insufficiently, correspond to an actual average, in particular when a restricted number of individual data are available as the normative database which were produced with an MRT device. Data are, for example, available in the literature on the average volume size of the different substances in different brain regions relative to age, gender, head size, etc., wherein these data are derived from a large number of investigated neurologically healthy individuals.

The resulting volumes are preferably compared statistically to the normative database and/or depicted as graphs.

These volumetric investigations allow individual brain regions of interest to be investigated with greater specificity. They are also based on the previously-performed voxel-based segmentation, although now they are defined by masks for brain regions. They are no longer voxel-based per se since a summation over all the voxels contained in the masks in each case has been performed.

In an alternative or additional further development of the method according to the invention, an additional test is advantageously performed to determine tissue damage, in particular a lesion load, wherein a three-dimensional mask is prepared in whose region the white or grey substance predominates, the values of the tissue maps are added separately in each case for the white and grey substance of the patient and of the data of the normative database for the region of the mask, and thus the volumetric values for the overall grey and white substance are thereby obtained within the mask for the patient and the normative database, and these are brought into relation with each other. This is in principle a volumetric examination wherein the overall regions—and not, however, the individual regions of the brain—are masked and examined in which the white substance or grey substance predominate in each case. It is thereby possible to determine the extent of the overall degeneration of the corresponding regions. Masking is preferably performed with reference to the tissue maps of the normative database.

This volumetric ratio directly correlates with the lesion load in the patient's brain. This is based on a model in which $GM_P$ is the volume of grey substance of a patient after using the classification method, $GM_N$ is the average volume of grey substance of the normative database after using a classification algorithm. WM stands for white substance, and CSF stands for cerebrospinal fluid (liquor). The index nomenclature of P and N is correspondingly the same as for GM.

The following formulas apply for the case in which the white substance forms the majority component. Since the contrast of the damage in the T1-weighted MRT images lies between that of the grey and white substance, it is assumed that the classification method overestimates the grey substance (minority component) and correspondingly underestimates the white substance. The liquor is not influenced. The amount of incorrectly classified white substance is identified as $\epsilon$. Accordingly $$GM_P = GM_N + \epsilon$$

$$WM_P = WM_N - \epsilon$$

$$CSF_P = CSF_N$$

The lesion load (LL) is defined as $$LL = \frac{GM_P}{WM_P}$$

The following first-order approximation accordingly applies $$LL \approx \frac{GM_N}{WM_N} + \frac{GM_N + WM_N}{WM_N^2} \cdot \epsilon$$

Consequently, LL directly correlates with the volumetric effect arising from the damage.

The object of the invention is also achieved by deploying a previously described method according to the invention for evaluating hypointense lesions in the white substance as represented by T1-weighted data in multiple sclerosis patients. By evaluating the apparent excess of grey substance in the regions of the white substance after segmentation, the method according to the invention functions as a statistically significant biomarker and can also be used to evaluate the extent and progression of the lesions.

The object of the invention is also achieved by a software program with program code means for processing MRT data of the human brain of a patient, wherein three-dimensional MRT data resolved in voxels of the patient's brain and brains of a normative database of a plurality of healthy human individuals are available, and when the program is run, at least step c) of the above described method according to the invention is implemented.

This software program is accordingly designed to perform at least the statistical analyses of the segmented tissue maps. Advantageously, in addition to the classification algorithm, a normalization algorithm and/or a smoothing algorithm is or are also implemented.

Finally, the object of the invention is also achieved by a system for processing MRT data of the human brain of a patient, wherein three-dimensional MRT data resolved in voxels of the patient's brain and brains of a normative database of a plurality of healthy human individuals are available, comprising a data processing system having a memory for the MRT data of the patient's brain, and the normative database, and for tissue maps on which the above-described software program according to the invention has been loaded. The method according to the invention can also be performed therewith.

The related subjects of the invention, i.e., the method, software program and system, have the same features, properties and advantages.

Further features of the invention will become apparent from the description of the embodiments according to the invention together with the claims and the included drawings. Embodiments according to the invention can fulfill individual features or a combination of several features.

BRIEF DESCRIPTION OF THE DRAWINGS

The invention will be described below without restricting the general inventive idea using exemplary embodiments with reference to the drawings, and for any details according to the invention which are not explained further in the text express reference is made to the drawings. In the figures.

DETAILED DESCRIPTION OF THE INVENTION

Figure 1:
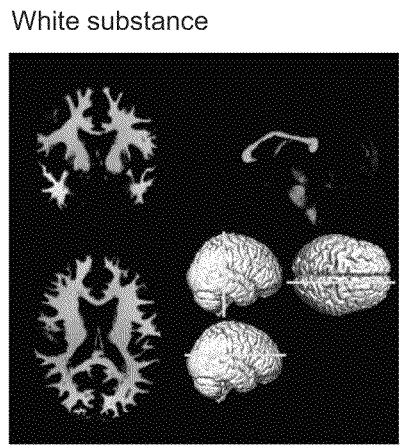
FIG. 1 shows tissue maps and statistical histogram representations of the grey substance, cerebrospinal fluid and white substance of a healthy patient, as well as comparisons with a normative database.
Figure 1:
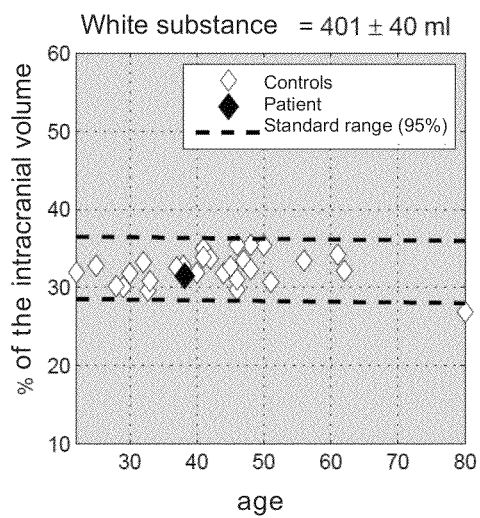
Figure 1:
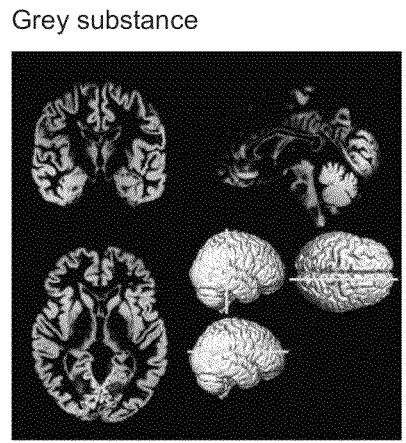
Figure 1:
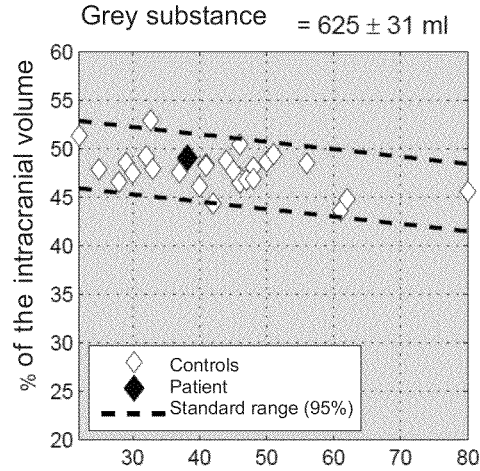
Figure 1:
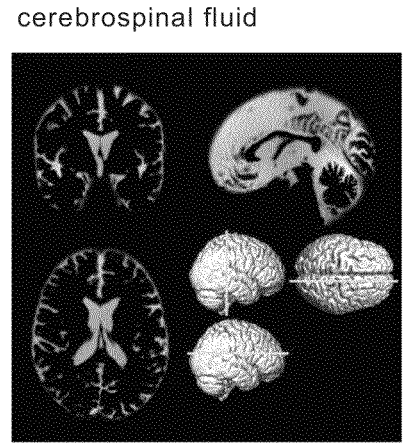
Figure 1:
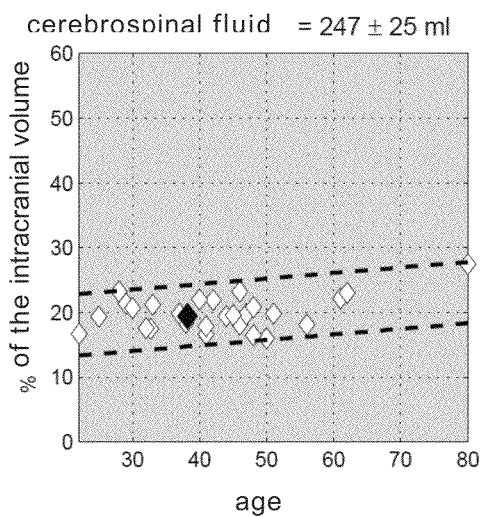

FIG. 1 shows typical sections of a brain, wherein the images of the tissue maps visualized in the left column depict grey substance (top), cerebrospinal fluid (middle) and white substance (bottom). A frontal section, sagittal section and a transverse section are depicted in each tissue map corresponding to the sections through the brain indicated by the bright sectional lines.

It can be seen that the grey substance predominates in the outer regions of the brain, the cerebrospinal fluid is located primarily in the central cavities and to the outside in the folds of the lobular regions, whereas the white substance represents the nerve pathways within the brain. For example, the optic nerve of an eye can also be clearly seen in the sagittal section of the white substance, FIG. 1, bottom left, right top image. The proportions of grey substance, white substance and cerebrospinal fluid are depicted in shades of grey that in each case correlate to the proportion of corresponding substance in the overall volume.

The tissue maps were prepared with the SPM8 software package by the Wellcome Trust Centre for Neuroimaging, London, Release April 2009, based on a publication by J. Ashburner et al., NeuroImage 26 (2005), pages 839 to 851 "Unified Segmentation".

The right column depicts histograms of the volumes assumed by the respective substances in the entire brain of grey substance, cerebrospinal fluid and white substance. The data point, i.e., the proportion expressed as the percentage of the intracranial volume of grey substance, cerebrospinal fluid and white substance of the patient, is depicted by a black dot, and the age of the patient is represented on the horizontal axis. White data points are the corresponding values for 27 individuals of the normative database who are between 20 and 80 years of age. The age-dependent $2\sigma$ standard range is depicted with dashed lines. This means that 95% of all healthy individuals lie within the ranges indicated by the dashed lines in terms of the overall volume of grey substance, cerebrospinal fluid and white substance. The patient with the brain or respectively tissue maps depicted in the left column also lies in the middle of this range. Furthermore, it can also be seen that the volume of grey substance decreases and is replaced by cerebrospinal fluid as age progresses.

Figure 2:
FIG. 2 shows a compressed depiction of transverse sections of a patient's brain, with identified clusters of statistically significant changed voxels.

FIG. 2 portrays a typical sequence of transverse sections through a patient's brain. The position of the sections is shown in the top left part of the figure. The brain and sections of the MRT scan are stereotactically normalized.

In the individual sections, regions with excess grey matter are identified in the region in which white matter predominates or respectively deficits of white matter in the same region. Such regions were examined or respectively masked for this analysis that have a predominance of white substance in the normative database. The excess grey matter which should hardly exist in this region results from misclassifications of damaged white substance and identifies regional damage of the white substance. This is enclosed by white lines. Regions with a deficiency of white substance which characterize regional thinning are represented by grey scale areas. A bright grey scale means a very high statistical probability of degeneration; darker grey areas are less statistically significant. These two statistical tests are graphically superimposed on the MRT scan and identify regional changes in the white substance.

In the central region of the brain and in the upper area of the right brain hemisphere, extensive regions can be seen in which a change has occurred.

Figure 3:
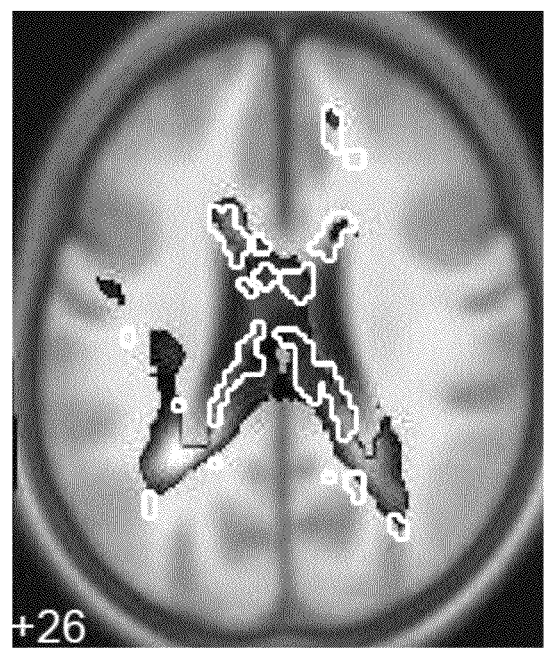
FIG. 3 shows an enlargement of an exemplary transverse section with z=+26 from FIG. 2.

An enlargement of one of these section images is shown in FIG. 3, i.e., at z=+26. In particular, it can be seen that the MRT images have been smoothed.

Figure 4:
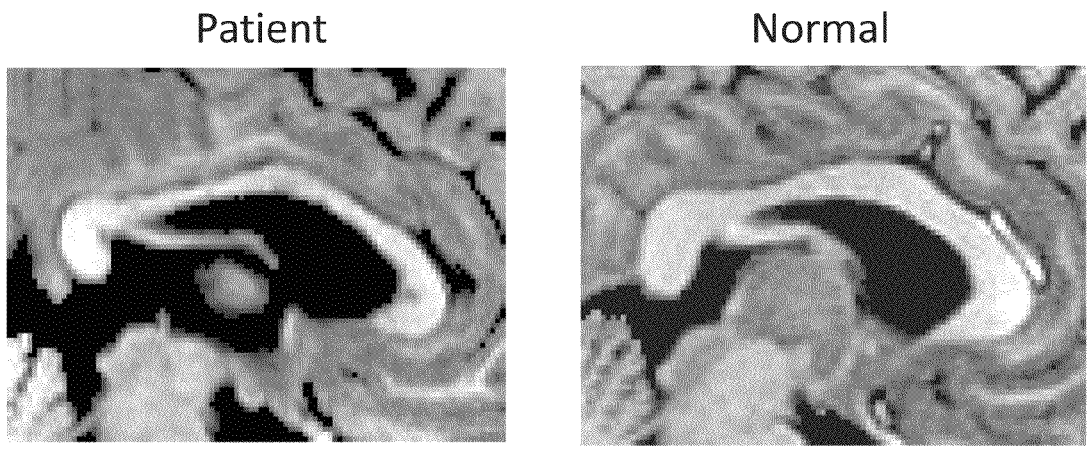
FIG. 4 shows a comparison of sagittal sections of a patient's brain and a healthy brain with an enlarged detail of the corpus callosum.

FIG. 4 shows adjacent enlarged sagittal sections of the corpus callosum of the left side of a patient's brain and the right side of a healthy patient (normal), wherein white substance with a bright appearance is clearly differentiated in the center from the surrounding grey substance and the cerebrospinal fluid in the center. The naked eye can recognize that the white substance in the diseased brain is significantly reduced in comparison to a normal or healthy brain. Degeneration has occurred here.

Figure 5:
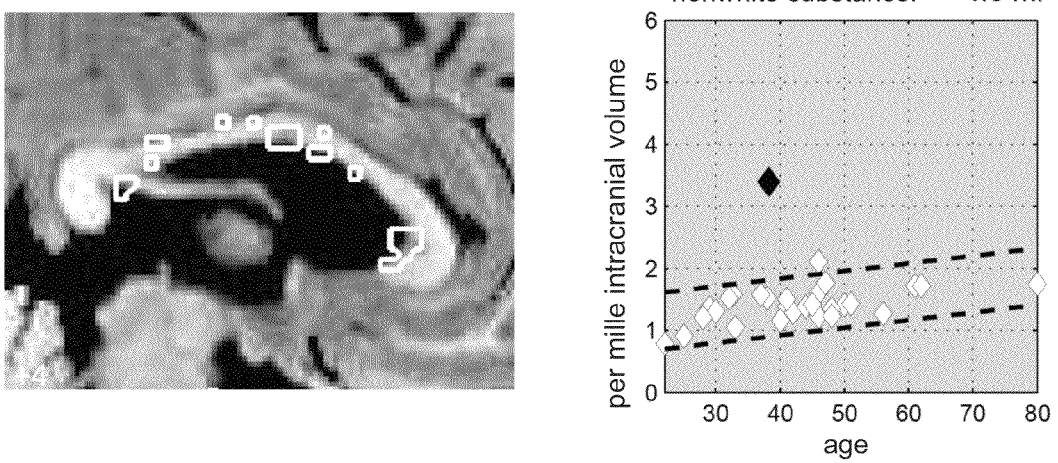
FIG. 5 shows sagittal sections of a degenerated corpus callosum with superimposed voxel clusters of regional damage and thinning with a statistical comparison of nonwhite substance and white substance.
Figure 5:
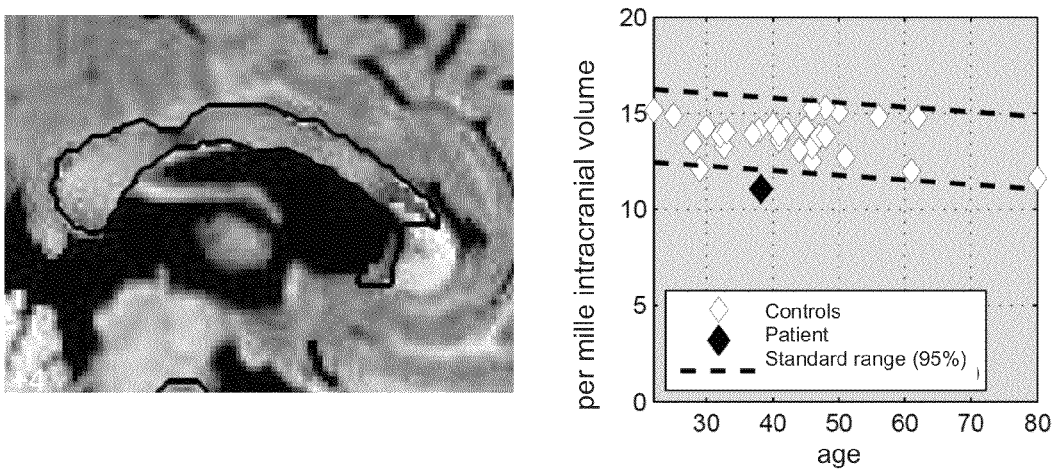

The left column in FIG. 5 shows the same region of the patient's brain as in FIG. 4, wherein clusters are marked in the top image in which excess grey substance was found, or respectively grey substance that resulted from the misclassification of diseased tissue. In the bottom image, a black line surrounds the region in which the corpus callosum has undergone a loss of white substance that should be located here. For this analysis, the corpus callosum was masked and accordingly selected using the data from the normative database, whereas the surrounding regions were not included.

The right column in FIG. 5 indicates the intracranial volume of non-white substance (top) and white substance (bottom) with a black data point in comparison to the normative database including the standard ranges of $\pm 2\sigma$ indicated by the dashed lines. It can, however, be clearly seen that the nonwhite substance in this region is overrepresented to a very statistically significant degree in the diseased patient. The volume of nonwhite substance in the corpus callosum refers to the entire intracranial volume in both images. The nonwhite substance in the corpus callosum should only be 1 to 2 per mille of the intracranial volume, whereas the white substance of the corpus callosum should be approximately 12 to 16 per mille of the entire intracranial volume. The decrease in white substance is not yet very statistically significant; it is approximately $3\sigma$ below the anticipated average. The increase in nonwhite substance is contrastingly highly statistically significant and is approximately 8 to $9\sigma$.

This information, especially the excess in nonwhite substance in a region in which white substance should actually predominate, represents a powerful biomarker for the degeneration of a brain.

Figure 6:
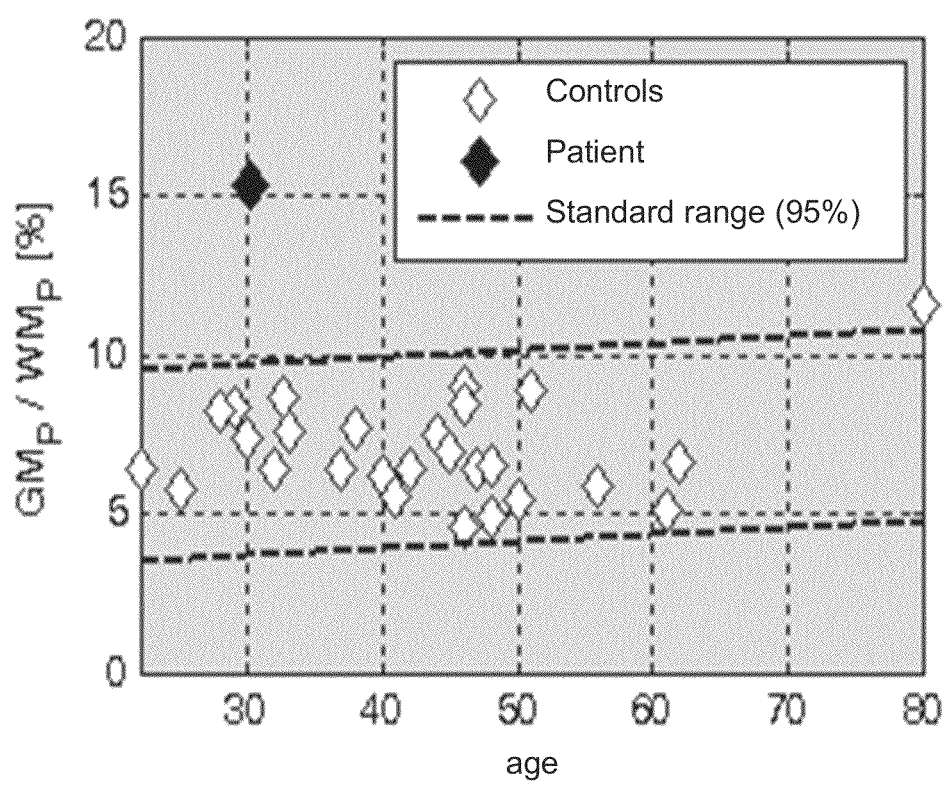
FIG. 6 shows a histogram representation of a lesion load of a patient compared to a normative database.

FIG. 6 shows a histogram that compares the lesion load (LL) for a patient's brain (black data point) to the data of the normative database (white data points). For regions in which the white substance predominates, the lesion load is defined as a ratio of the grey substance to the white substance in the correspondingly masked patient data. In this case as well, it can be seen that the lesion load of the patient is significantly elevated above that of the normative database for the same region.

All of the cited features including those to be taken from the drawings alone, as well as individual features that are disclosed in combination with other features, are considered essential to the invention by themselves and in combination. Embodiments according to the invention can be realized by the individual features, or a combination of several features.

The invention claimed is:

1. A method for processing MRT data of a brain of a patient, wherein three-dimensional MRT data resolved in voxels of the brain of the patient and brains of a normative database of a plurality of neurologically healthy human individuals are available, comprising the steps of:
    segmenting the MRT data of the brain of the patient for each voxel into portions of grey substance, white substance and liquor by way of a classification algorithm,
    transforming the data to be compared with corresponding data of the normative database into a standardized stereotactic space, resulting in one or more normalized tissue maps that contain proportions determined by the classification algorithm, wherein the transformation occurs before, after or synchronous with segmentation, and
    subjecting the tissue map or tissue maps of the brain of the patient to a voxel-wise statistical comparison with correspondingly normalized and segmented data of the normative database,
    wherein the voxel-wise statistical comparison of the tissue map, or tissue maps, is a morphometric comparison, wherein statistically significant voxels in the tissue map, or tissue maps, of the brain of the patient are identified that belong to a region dominated by the white substance that contains more grey substance than should be expected from the normative database, or that belong to a region dominated by the grey substance that contains more white substance than would be expected from the normative database.

2. The method according to claim 1, wherein, in addition, such statistically significant voxels are identified in the tissue map, or tissue maps, of the brain of the patient that belong to a region dominated by the white substance in which less white substance is contained than is to be expected from the normative database, or that belong to a region dominated by the grey substance in which less grey substance is contained than is to be expected from the normative database.

3. The method according to claim 1, wherein coherent clusters of statistically significant voxels are measured and/or counted and/or depicted as a histogram with reference to their volume.

4. The method according to claim 1, wherein the segmented MRT data is smoothed to create the tissue map or tissue maps.

5. The method according to claim 1, wherein patterns arising from the voxel-wise statistical comparison are imaged.

6. The method according to claim 1, wherein voxels of the tissue map, or tissue maps, are interpolated into regular or irregular grids.

7. The method according to claim 1, wherein parameters of the classification algorithm are iteratively adjusted to reproduce published results for the MRT data of the normative database and/or finely adjusted to a ground truth of simulated data, wherein the classification algorithm for the voxel-wise statistical comparison is used with same parameters for the MRT data from the normative database as well as from the brain of the patient.

8. The method according to claim 1, wherein one or more volumetric tests are performed additionally in which volumes of white and grey substance can be calculated from the tissue maps using masks for regions of the brain of the patient to be examined.

9. The method according to claim 8, wherein the volumes are adapted to individual data of the patient by way of a correction with respect to a covariate, or a plurality of covariates, including head size, age, duration of illness and/or gender, and/or are standardized to an overall brain substance, overall white or grey substance, or overall intracranial volume.

10. The method according to claim 9, wherein the adapted volumes are corrected for age.

11. The method according to claim 8, wherein the volumes are statistically compared against the normative database and/or depicted as graphs.

12. The method according to claim 1, wherein an additional test is performed to determine tissue damage wherein a three-dimensional mask is prepared in whose region the white or grey substance predominates, a value of the tissue maps are added separately in each case for the white and grey substance of the patient and data of the normative database for the region of the mask, and thus volumetric volumes for an overall grey and white substance are thereby obtained within the mask for the patient and normative database in each case, and these are brought into relation with each other.

13. The method according to claim 12, wherein the tissue damage is a lesion load.

14. The method according to claim 1, wherein said method is used for evaluating hypointense lesions in the white substance as depicted in T1-weighted data for multiple sclerosis patients.

15. A non-transitory computer readable medium stored with a computer program, that when executed by a computer, causes the computer to process MRT data of a brain of a patient, wherein three-dimensional MRT data resolved in voxels of the brain of the patient and brains of a normative database of a plurality of healthy human individuals are available, and when the computer program is run, performs steps comprising:
    segmenting the MRT data of the brain of the patient for each voxel into portions of grey substance, white substance and liquor by way of a classification algorithm,
    transforming the data to be compared with corresponding data of the normative database into a standardized stereotactic space, resulting in one or more normalized tissue maps that contain proportions determined by the classification algorithm, wherein the transformation occurs before, after or synchronous with segmentation, and
    subjecting the tissue map or tissue maps of the brain of the patient to a voxel-wise statistical comparison with correspondingly normalized and segmented data of the normative database,
    wherein the voxel-wise statistical comparison of the tissue map, or tissue maps, is a morphometric comparison, wherein statistically significant voxels in the tissue map, or tissue maps, of the brain of the patient are identified that belong to a region dominated by the white substance that contains more grey substance than should be expected from the normative database, or that belong to a region dominated by the grey substance that contains more white substance than would be expected from the normative database.

16. The non-transitory computer readable medium stored with a computer program according to claim 15, wherein, in addition to the classification algorithm, a normalization algorithm and/or a smoothing algorithm is or are implemented.

17. A system for processing MRT data of a brain of a patient, wherein three-dimensional MRT data resolved in voxels of the brain of the patient and brains of a normative database of a plurality of healthy human individuals are available, comprising a data processing system having a memory for the MRT data of the brain of the patient, and the normative database, and for tissue maps on which non-transitory computer readable medium stored with a computer program that is programmed to:
- segment the MRT data of the brain of the patient for each voxel into portions of grey substance, white substance and liquor by way of a classification algorithm,
- transform the data to be compared with corresponding data of the normative database into a standardized stereotactic space, resulting in one or more normalized tissue maps that contain proportions determined by the classification algorithm, wherein the transformation occurs before, after or synchronous with segmentation, and
- subject the tissue map or tissue maps of the brain of the patient to a voxel-wise statistical comparison with correspondingly normalized and segmented data of the normative database,
- wherein the voxel-wise statistical comparison of the tissue map, or tissue maps, is a morphometric comparison, wherein statistically significant voxels in the tissue map, or tissue maps, of the brain of the patient are identified that belong to a region dominated by the white substance that contains more grey substance than should be expected from the normative database, or that belong to a region dominated by the grey substance that contains more white substance than would be expected from the normative database.

* * * * *